Figure 1:
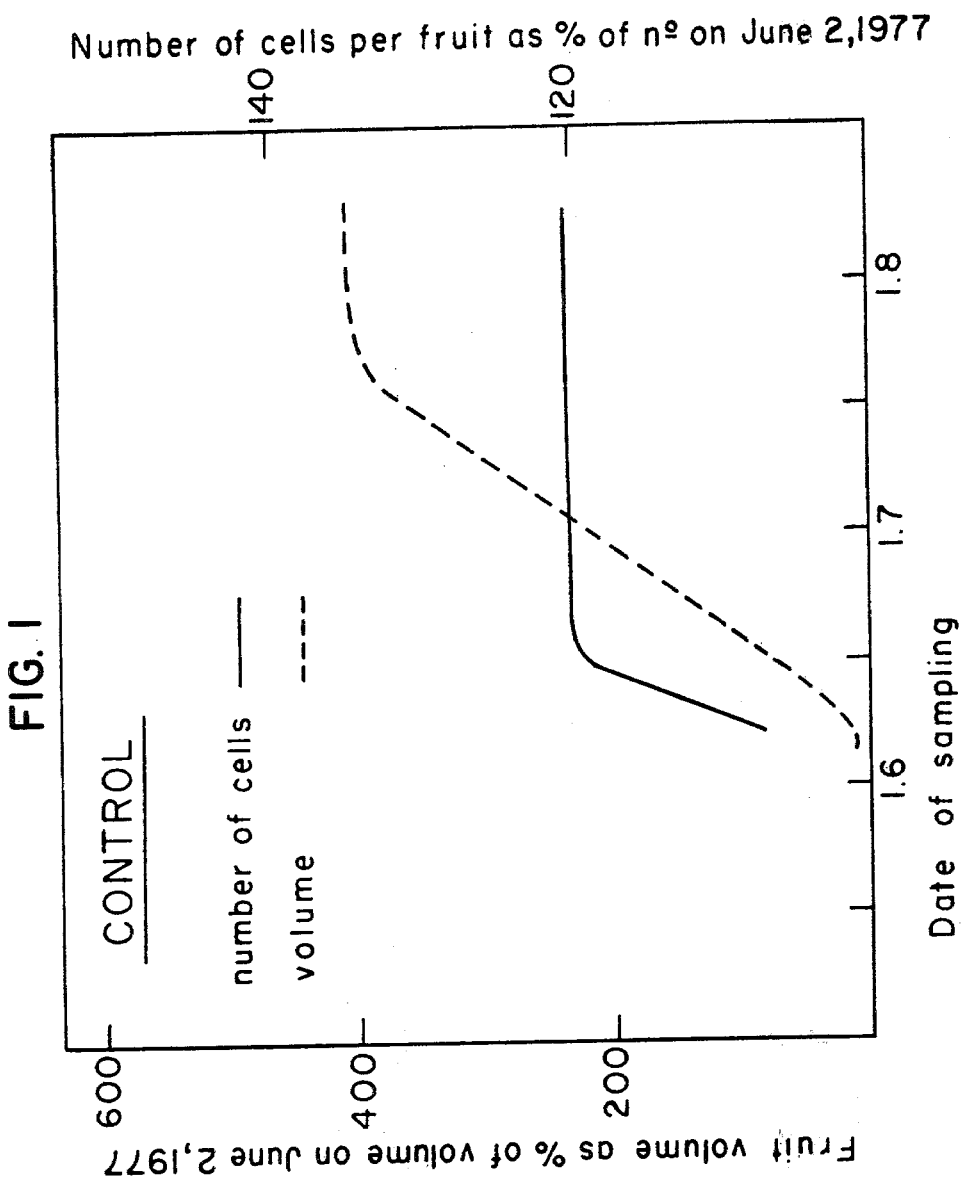

United States Patent [19]

Kessler

[11] 4,309,205

[45] Jan. 5, 1982

[54] ENHANCEMENT OF REPRODUCTIVE PLANT DEVELOPMENT BY MEANS OF CHOLINE SALTS

[75] Inventor: Bezalel Kessler, Rehovot, Israel

[73] Assignee: The State of Israel Ministry of Agriculture, Israel

[21] Appl. No.: 180,907

[22] Filed: Aug. 25, 1980

[30] Foreign Application Priority Data

Aug. 27, 1979 [IL] Israel .................................. 58112

[51] Int. Cl.³ .............................................. C05G 3/00
[52] U.S. Cl. ......................................... 71/27; 71/64.1; 71/121
[58] Field of Search ...................... 71/1, 11, 27, 64 C, 71/121, 64.8, 64.10

[56] References Cited

FOREIGN PATENT DOCUMENTS 1441422  5/1966  France .................................. 71/121

Primary Examiner—S. Leon Bashore
Assistant Examiner—Ferris H. Lander
Attorney, Agent, or Firm—Steinberg & Raskin

[57] ABSTRACT

The reproductive development of plants is enhanced by application of non-toxic choline salts in aqueous medium. The application may be via the root system or by spraying. If desired a free radical scavenger may be applied together with the choline salts.

8 Claims, 3 Drawing Figures

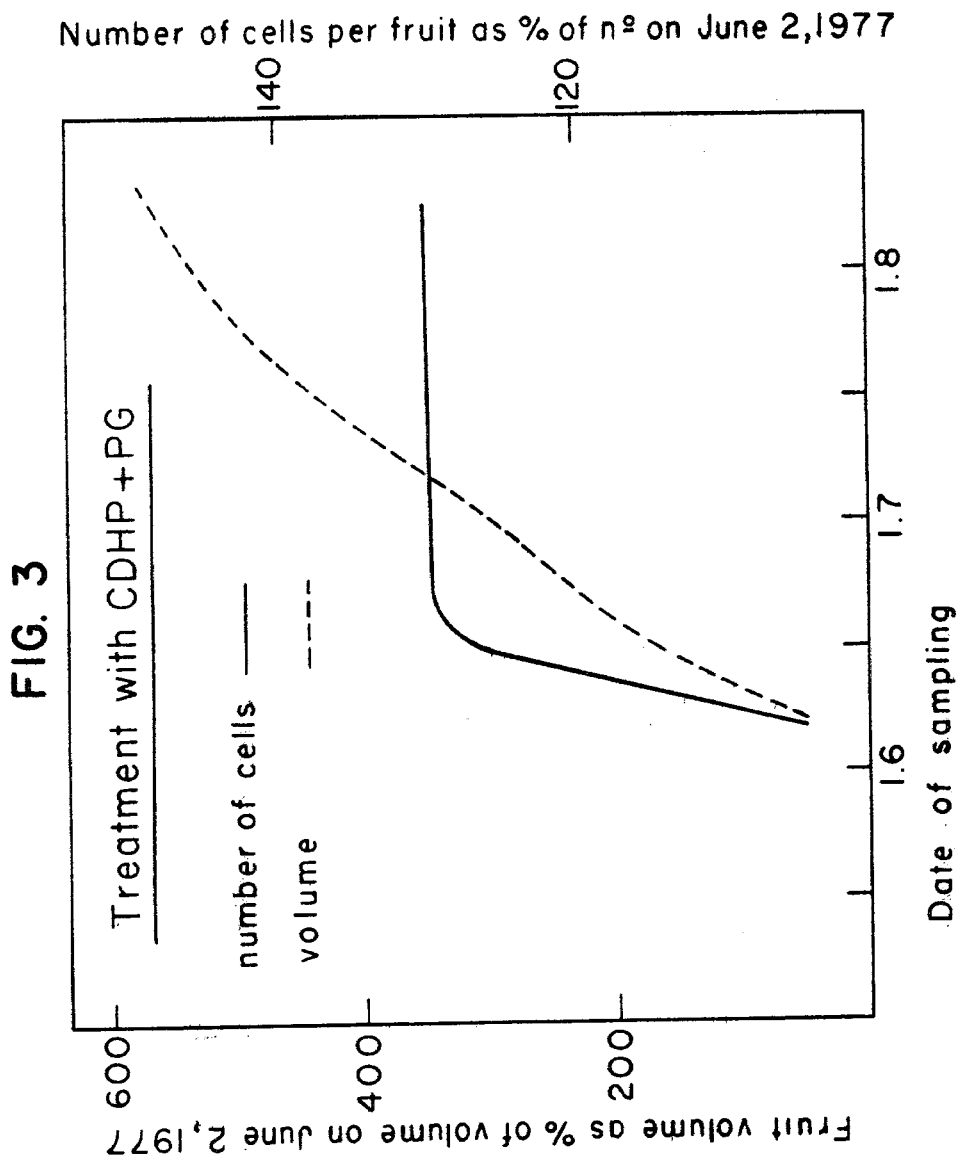

ENHANCEMENT OF REPRODUCTIVE PLANT DEVELOPMENT BY MEANS OF CHOLINE SALTS

The present invention concerns a method and means for enhancing the reproductive development of plants, i.e. for increasing the quantity and/or improving the quality of flowers and fruits.

The reproductive development of plants is regulated by interactions between environmental and internal factors and such interaction may be mediated and thereby enhanced by so-called plant development regulators that are man-applied to the plants. The regulation of the reproductive development of plants in horticulture and agriculture is increasingly gaining in importance.

In accordance with the present invention it has surprisingly been found that choline salts are capable of enhancing the reproductive development of plants. Choline is an organic base having the formula $[(CH_3)_3N^+CH_2CH_2OH]OH^-$ and it is capable of forming salts with organic and inorganic acids.

The invention thus comprises a method of enhancing the reproductive development of plants growing on soil comprising applying to the plant an effective amount of at least one non-toxic choline salt in aqueous medium.

The application of choline salts to plants in accordance with the invention may be via the root system by way of irrigation or foliar by way of spraying, and the salts are used in form of aqueous solutions or dispersions such as colloidal solutions. Where the application is via the root system the choline salt may be incorporated, suitably dosed, in irrigation water, if any, or an aqueous fertilizer solution or dispersion, if any. In case of application via the root system, the annual amount of choline salt applied to the soil should preferably not exceed 500 kg/hectare. For foliar application the annual amount of sprayed choline salt will be of the order of 30 kg/hectare and aqueous solutions or dispersions may be used that contain 1% by weight or more of choline salt.

The salts employed in accordance with the invention may be organic or inorganic. The requirement that they should be non-toxic is to be understood as meaning that the choline salts used should neither be phytotoxic nor toxic to animals and humans in the concentration ranges in which they are used. Examples of salts suitable for the performance of the method according to the invention are choline dihydrogen phosphate and choline dihydrogen citrate.

Choline and its salts are known compounds but their use for the regulation of the reproductive development of plants has not yet been investigated. G. Wyn Jones and M. Scott reported in "New Method For pH Control in Ornamentals", The Grower, May 3, 1975, p. 938/9, that when Azalea and Hydrangea were grown on peat compost in containers with alkaline water supply and choline dihydrogen phosphate was added to the peat compost, the pH of the compost, which was initially 5.4, was lowered to and retained at 4.7 while in untreated controls it rose to 6.3. In Azaleas the authors further observed that while in untreated plants the alkalinity of the irrigation water reduced the quality of the plants, no such reduction occurred in treated plants. At the same time the nitrogen and phosphate levels in the leaves of treated plants increased to two- to threefolds of the normal value. It is thus evident that the disclosure by Wyn Jones et al. concerns essentially the restoration of Azalea nursery stock grown in pots under alkaline conditions to their normal shape and size by a treatment which essentially cancels out an adverse effect of the otherwise alkaline conditions at which the nursery plants were raised.

Similar experiments were reported by R. G. Wyn Jones in "A Possible New Method for Improving Plant Growth in Saline and Calcaerous Environments", Isotopes and Radiation in Soil-Plant Relationship including Forestry, I.A.E.A, 1972, p. 109–122, and by R. Gareth Wyn Jones, Anthony J. Rippin and Richard Storey in "Metabolism of Choline in Rhizosphere and its Possible Influence on Plant Growth", Pestic. Sci. 4, 375–383. They found that when 3-day old seedlings of Zea mays were potted in culture vessels containing a so-called Long Ashton Medium or an artificial calcaerous soil culture, to which various salts were added and whose pH was in some cases adjusted to 7.8 and in others to about 5.8, the addition of choline chloride caused a pH drop of 1.5 to 2.0 pH units and overcame to some extent the otherwise growth inhibitory effects of the salinity and alkalinity of the growth medium.

These experiments concerned potted seedlings in the nursery stage potted in alkaline or saline unnatural growth medium. In distinction therefrom the present invention concerns the treatment of mature plants in the reproducing stage, grown on natural soil in orchards and fields. In accordance with the invention the pH of the soil, in the recommended concentration ranges remains essentially unchanged even where the application of choline salt is via the root system, probably because of the superior buffering activity of the soil.

It is thus evident that none of the teachings in any of the above publications could have suggested in any way to the man of the art the present invention and the invention is distinguished from those teachings in an unexpected and surprising way.

In accordance with the present invention it is possible to use the choline salts by themselves or in combination with at least one compound selected from the group known as free radical scavengers (hereinafter "FRS"). Examples of such compounds are nickel nitrate, nickel chloride, cobalt nitrate, cobalt chloride, nickel potassium nitrite, cobalt potassium nitrite, cobalt potassium sulfate, nickel potassium sulfate, butylated hydroxyanisol, butylated hydroxytoluene, citric acid, $\alpha$-tocopherol, propyl gallate. This is of course a non-exhaustive list of examples only and many other organic and inorganic compounds fall into this group. The feature common to all these compounds is that they prevent the activity of free radicals and because of this capacity members of the group are commonly used as food preservatives. To the best of the inventor's knowledge they have never before been used for enhancing the reproductive development of plants.

The invention also provides choline salt compositions for use in the performance of the above method. Such compositions may also contain an FRS and they may be in the form of dilute or concentrated aqueous solutions or dispersions of at least one choline salt. They may also be in the form of dry mixtures of at least one choline salt with at least one FRS substance.

The method according to the invention is applicable to a large variety of plants, for example deciduous fruit trees such as apple, pear, plum and peach trees; subtropical trees such as citrus, pecan, olive and avocado trees; banana plants; vegetables and other field growths such as cucumbers, tomatoes, gourds, melons, marrow, lettuce, carrots, pepper, and cotton; cereals such as corn;

and various ornamental plants such as roses, carnations, immortal, riscus and hortensia. This list is by way of example only and is in no way exhaustive.

The beneficial effects attainable in accordance with the invention comprise:

1. Increase in fruit size and total yield. For example, in some apple varieties the size of the apples was almost doubled upon treatment in accordance with the invention.

2. Regulation of relative duration of cell division and enlargement phases of fruit development which determines the texture and the storage qualities of the fruit.

3. Increase in colour intensity and area of background colour in coloured fruit, e.g. coloured apple varieties.

4. Highly significant decrease in pitting, e.g. bitter pit in apples. Bitter pit in apples is a major and severe post-harvest disorder in many countries where apples are grown, e.g. in the U.S.A., South Africa and Australia, and damage may reach even 30% of the total crop making the affected fruit unsuitable for marketing and export. It has been reported that the severity of this disorder may be reduced to some extent by 6-8 sprays with a calcium nitrate solution, but this treatment is of rather limited value in addition to being expensive. Treatments in accordance with the invention are much cheaper, more effective and easy to carry out.

5. Break of dormancy. The break of dormancy is an old but still not fully solved problem. In horticultural practice emulsions of mineral oil, to which dinitro-orthocresol (or other chemicals of similar nature) is added, is still the recommended and most popular treatment to break dormancy commercially in deciduous trees. This treatment is quite often only partially successful, in particular in warm winters. In accordance with the invention the shortcomings of known treatments are successfully overcome.

6. Prevention of sun burn, i.e. fruit damages by high solar irradiation. Some fruit varieties, such as, for example, the apple cultivar Granny Smith, are highly sensitive to an exposure to strong sun light, producing lesions in the fruit which markedly reduce their marketability. By one known method some partial protection is achieved by covering the trees with plastic nets. By another known technique the fruits are sprayed with lime which after harvest must be washed off. These known methods are costly and highly inconvenient. In accordance with the invention it has been found that sun burns are effectively and significantly prevented by spraying a choline salt on the fruit, preferably in admixture with an FRS, whereby the resistance of the fruit to strong sun light is markedly increased and the occurrence of so-called sun burn in the fruit is markedly reduced.

For the application of a choline salt via the roots of plants in accordance with the invention an aqueous solution or dispersion of the salts, if desired in combination with one or more FRS, may be injected into irrigation pipes or via fertilizer drums connected to an irrigation system, e.g. trickle or sprinkler systems. The aqueous solutions or dispersions employed may contain about 50% by weight of active material and the amount of such solution may be about from 200 to 300 liters per hectare, the exact amount varying in accordance with specific requirements. This amount may be given in intervals, e.g. weekly, by means of several separate irrigation runs, e.g. 5 irrigations of 50-60 liters each in the early spring time.

Where in accordance with the invention a choline salt is applied by spraying, if desired, in combination with one or more FRS, the concentration of the spray solution or dispersion and the regime of application will be selected in dependence on the nature of the cultavar and the specific requirements.

Some tests in which choline dihydrogen phosphate (CDHP) was applied to three different apple varieties via the roots are summed up in the following table I. The table shows the cumulative effect of five treatments on 25/5, 31/5, 2/6, 12/6 and 15/6 of 1978. On each occasion 60 liters of an aqueous solution containing 50% by weight of CDHP was applied via a fertilizer drum per hectare over a period of 90 minutes. The total amount of irrigation was 50 m$^3$ per day per hectare. The treatment was given in randomized blocks. Each treatment comprised 8 replicates, each replicate being composed of 10 trees.

Pursuant to the treatment the yield, size, colour index and bitter pit of the applies were observed at the following times:
(i) size, yield and colour were measured at harvest time (August to September, according to variety);
(ii) bitter pit was evaluated three months after harvest of fruit from cold storage.

The size of the fruit is expressed in terms of the diameter. The colour effect is expressed in the colour index which is the expression "colour intensity×% background colour". The colour intensity is determined by reference to a recognised colour chart or atlas and the percentage background colour is the percentage of the area out of the total that shows the background colour.

TABLE I

The effect of CDHP on the yield and quality of some apple varieties

| Variety | Treatment | Yield ton/h | Large-sized fruit (as % of total yield) | | Colour Index (colour intenxity × % background colour) | Bitter pit (% of total number of fruits) |
|---|---|---|---|---|---|---|
| | | | 55-60mm diameter | 65-75mm diameter | | |
| Jonathan | C | 24 | 32 | 56 | 4 | 0.65 |
| | T | 35* | 27 | 65* | 15** (red colour over 50%) | 0.32** |
| Golden Delicious | C | 45 | 54 | 12 | — | 17.00 |
| | T | 45 | 67* | 23** | — | 7.00** |
| Granny Smith | C | 32 | 43 | 12 | — | — |
| | T | 40* | 45 | 28** | — | — |

*p = 0.05
**p = 0.01

In the above table C=control, T=treatment and p stands for statistic significance (the smaller p the higher the significance).

From the foregoing table I the beneficial effects of the treatment according to the invention on the yield, the size of the fruit, the colour index and the reduction of bitter pit are clearly visible.

In the following table II some test series are summed up demonstrating the effects of a treatment according to the invention on the break of dormancy of apple trees of the Golden Delicious variety. The tests were carried out in winter 1979. In the series of control tests a spray mixture was used comprising a commercial narrow range winter oil (a mineral oil fraction) containing 2,4-dinitro-ortho-cresol. In a first series of tests according to the invention 2,4-dinitro-ortho-cresol in the spray mixture was replaced by 1% by weight aqueous solution of choline dihydrogen phosphate (CDHP). In a second series of tests according to the invention propyl gallate (PG) was also added in an amount of 0.12% by weight and in a third series of tests according to the invention cobalt chloride (CC) in an amount of 0.2% by weight was added instead of PG. Both PG and CC are free radical scavengers. The time of application was in the middle of March by means of one single spray in the amount of from 5 to 10 liters per tree.

TABLE II

The effect of CDHP and FRS agents on the break of dormancy of apple trees var. Golden Delicious in winter 1979.

| Treatment | | Number of apical branches with full break of dormancy, i.e., full coverage with leaves (in % of the 200-250 apical branches counted per treatment) |
|---|---|---|
| Control - Conventional spray | | 21 |
| CDHP | According to invention | 44* |
| PG additive | According to invention | 52* |
| CC additive | According to invention | 48* |

*p = 0.01

It is seen from the above that the treatment with CDHP alone according to the invention more than doubles the break of dormancy effect and that this effect is further enhanced by the addition of FRS substances such as propyl gallate and cobalt chloride.

Table III illustrates the effect of a spraying treatment according to the invention for preventing sun irradiation damages to Granny Smith apples. For spraying an aqueous solution was used containing 1% by weight of choline dihydrogen phosphate (CDHP) and a 100 ppm of cobalt chloride (CC).

TABLE III

Protective Effects of CDHP and FRS Agents against high-intensity sun irradiation damages (sun burn) in apples.

| Treatment | % Apples with sun-burn | Yield of "clean" apples, ton per hectar |
|---|---|---|
| Control | 16 | 14 |
| C76 | 7 | 28 |

It is seen from the above Table III that upon treatment in accordance with the invention the damage was less than half of that of the untreated control, while the yield of undamaged, "clean" apples was doubled.

In the following table IV the effect of a spraying treatment in accordance with the invention on the break of dormancy in peach trees is demonstrated. Aqueous solutions containing 1% by weight of choline dihydrogen phosphate (CDHP) and choline dihydrogen citrate (CDHC) were used. A significant improvement as compared to the control is noted in both cases.

TABLE IV

Effects of spraying treatments with CDHP and CDHC on the break of dormancy in peaches

| Treatment | Bud Opening (%) | |
|---|---|---|
| | Terminal | Lateral |
| Control | 51.2 ± 3.4 | 12.5 ± 4.9 |
| CDHP | 76.2 ± 8.1 | 48.7 ± 3.6 |
| CDHC | 66.5 ± 6.5 | 25.0 ± 5.1 |

The beneficial effects achieved in accordance with the invention have also been demonstrated on pecan trees. The lack of filling of pecan nuts and the low total net yield of high quality nuts restricts severely the rentability of pecan orchards in all pecan growing countries such as the U.S.A., South Africa and Israel. As shown in the following table V treatment in accordance with the invention was found both to increase the size of the nuts and their quality expressed in terms of filling. The treatment was by spraying of an aqueous solution containing 1% by weight of choline dihydrogen phosphate (CDHP) and 50 ppm of cobalt chloride (CC). In the Table A, B and C are conventional designations for size grades: A—very large, B—large, C—small. Again a significant improvement over the control is noted.

TABLE V

The Effect of CDHP and CC as on the yield and quality of pecan nuts var. Delmas, 1978

| Treatment | Net yield (kg per tree) | Nut size (as % of total yield) | | | Degree of filling of nut A size | | |
|---|---|---|---|---|---|---|---|
| | | A | B | C | A | B | C |
| Control | 60 | 24 | 33 | 43 | 12 | 83 | 5 |
| CDHP + CC | 89 | 63 | 16 | 21 | 30 | 70 | 0 |

In the following table VI the effects of spraying treatment in accordance with the invention are demonstrated. The treatment was by spraying of an aqueous solution containing 0.5% by weight of choline dihydrogen phosphate (CDHP) and 0.05% by weight of cobalt chloride (CC). In the table the weight and colume are stated in terms of percentage control. It is seen that with the exception of "Experimental" Nectarine variety the treatment brought about a significant improvement.

TABLE VI

Effects of spraying treatments with CDHP and CC on the volume and weight of stone fruits (in % of control)

| Species | Variety | Treatment with CDHP + CC | |
|---|---|---|---|
| | | Weight | Volume |
| Plum | Sweet Elinor* | — | 132 |
| | Shiper | 128 | 139 |
| Nectarine | Experimental | 80 | 87 |
| | 44/28 | 114 | 114 |
| Peach | 16/33 | 113 | 108 |
| | 13/72* | 122 | 118 |

*Early spring varieties.

The invention is further illustrated in the accompanying drawings which are graphical representations showing the effects of treatments according to the invention on cell multiplication and cell growth in Jonathan variety apples.

Figure 2:
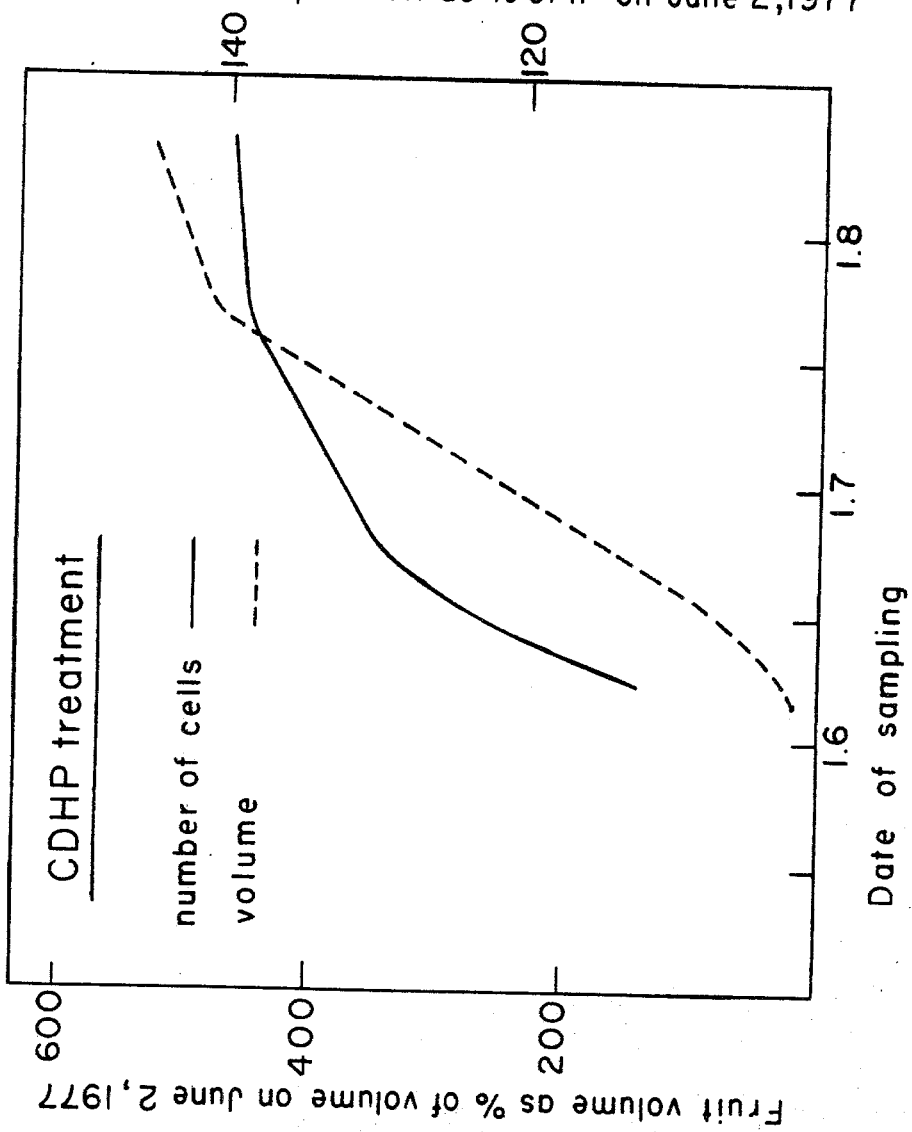

In the drawings:

FIG. 1 is a plotting of the fruit volume and number of cells against time of sampling for untreated controls;

FIG. 2 is a similar plotting for fruit treated in accordance with the invention by spraying with an aqueous 0.5% by weight choline dihydrogen phosphate (CDHP) solution; and FIG. 3 is a similar plotting for fruit treated by spraying in accordance with the invention with an aqueous solution containing 0.5% by weight of CDHP and 0.1% by weight of propyl gallate (PG).

In the figures the treatment points are expressed in terms of percentage of reference fruit picked on June 2, 1977.

It is seen from FIG. 1 that with untreated fruit the number of cells remained constant after about mid-June while the volume continued to increase only about mid-July.

From FIG. 2 it is seen that pursuant to a spraying treatment with CDHP alone both the number of cells and the volume continued to increase only mid-July and the volume increased even thereafter though at a lower rate.

FIG. 3 shows that upon the spraying treatment with CDHP and PG the number of cells remained constant after about mid-June but their absolute number was higher (130% of reference) than with the control (120% of reference). Against this the volume continued to rise steadily for the duration of the measurements.

I claim:

1. A method of increasing the quantity and quality of flowers and fruits of plants growing in soil, which comprises applying to mature plants during its reproductive stage a flower or fruit quantity and quality improving effective amount of at least one non-toxic salt of choline in aqueous medium.

2. A method according to claim 1, wherein said salt of choline is applied in combination with at least one compound selected from the group of free radical scavengers.

3. A method according to claim 1, wherein said salt of choline is applied via the roots in the form of an aqueous solution or dispersion.

4. A method according to claim 3, wherein the annual amount of said salt of choline applied to the soil does not exceed 500 kg/hectar.

5. A method according to claim 1, wherein said salt of choline is selected from the group consisting of choline dihydrogen phosphate and choline dihydrogen citrate.

6. A method according to claim 1, wherein said salt of choline is applied by the foliar route by spraying.

7. A method according to claim 6, wherein the amount of said sprayed salt of choline does not exceed 30 kg/hectar.

8. A composition of matter suitable for the performance of the method according to claim 1, comprising water and a flower or fruit quantity and quality improving effective amount of at least one non-toxic salt of choline and at least one free radical scavenger.

* * * * *